(12) United States Patent
Klasek et al.

(10) Patent No.: US 9,440,040 B2
(45) Date of Patent: Sep. 13, 2016

(54) HUMIDIFIER FOR RESPIRATORY APPARATUS

(75) Inventors: Paul Jan Klasek, Bella Vista (AU);
Alexander Virr, Bella Vista (AU);
Ronald James Huby, Bella Vista (AU);
Jack Wei Cheng, Bella Vista (AU)

(73) Assignee: ResMed Limited, Bella Vista (AU)

( * ) Notice: Subject to any disclaimer, the term of this patent is extended or adjusted under 35 U.S.C. 154(b) by 1729 days.

(21) Appl. No.: 12/312,207

(22) PCT Filed: Nov. 8, 2007

(86) PCT No.: PCT/AU2007/001715
§ 371 (c)(1),
(2), (4) Date: Apr. 30, 2009

(87) PCT Pub. No.: WO2008/055307
PCT Pub. Date: May 15, 2008

(65) Prior Publication Data
US 2009/0320840 A1    Dec. 31, 2009

(30) Foreign Application Priority Data

Nov. 8, 2006    (AU) ................................ 2006906224

(51) Int. Cl.
*H05B 3/34* (2006.01)
*H05B 3/54* (2006.01)
(Continued)

(52) U.S. Cl.
CPC ..... *A61M 16/1075* (2013.01); *A61M 16/0875* (2013.01); *A61M 16/1095* (2014.02);
(Continued)

(58) Field of Classification Search
CPC ............. A61M 16/16; A61M 16/161; A61M 16/162; A61M 16/164; A61M 16/165; A61M 16/167; A61M 16/168

USPC ........... 128/203.26, 203.16, 203.17, 203.27, 128/204.14, 204.17, 200.11, 200.12, 128/200.13, 911, 912; 392/303, 469, 470, 392/325; 219/549, 539
See application file for complete search history.

(56) References Cited

U.S. PATENT DOCUMENTS 1,839,234 A  *   1/1932  Lehn ............................. 261/153
2,429,112 A  *  10/1947  Warren ......................... 392/325
(Continued)

FOREIGN PATENT DOCUMENTS

WO          97/15344         5/1997
WO       WO 9915862 A1 *    4/1999

OTHER PUBLICATIONS

International Search Report for PCT/AU2007/001715, mailed Mar. 14, 2007.

*Primary Examiner* — Peter S Vasat
(74) *Attorney, Agent, or Firm* — Nixon & Vanderhye P.C.

(57) ABSTRACT

A flexible tape heater (110) in a patient conduit (112) may be used to heat the flow of gas in the patient conduit (112) that is delivered to the patient mask (116). The thin, flat and extended nature of the flexible tape heater (110) may enhance heat transfer with the gas flow while also providing low impedance to the gas flow. Heating of the gas may facilitate the desired temperature and humidity to be reached for the gas delivered to the patient by the respiratory apparatus. The flexible tape heater (110) may be placed in the patient conduit (112) such that the flexible tape heater (110) is twisted or bent about one or more of the flexible tape heater's (110) three axes. Additionally these configurations may be used to enhance the turbulent mixing of the water vapor produced in the humidification chamber (114) with the gas flow.

82 Claims, 10 Drawing Sheets

(51) Int. Cl.
*H05B 3/56* (2006.01)
*H05B 3/58* (2006.01)
*A61M 16/10* (2006.01)
*A61M 16/16* (2006.01)
*A61M 16/08* (2006.01)
*A61M 16/00* (2006.01)

(52) U.S. Cl.
CPC .......... *A61M16/16* (2013.01); *A61M 16/0816* (2013.01); *A61M 2016/0027* (2013.01); *A61M 2205/14* (2013.01); *A61M 2205/3368* (2013.01); *A61M 2205/3375* (2013.01); *A61M 2205/6018* (2013.01); *A61M 2205/6054* (2013.01); *A61M 2230/04* (2013.01)

(56) References Cited

U.S. PATENT DOCUMENTS

| | | | | |
|---|---|---|---|---|
| 2,617,010 | A * | 11/1952 | Schmitz | 392/324 |
| 3,309,503 | A * | 3/1967 | Dow et al. | 392/369 |
| 3,687,130 | A * | 8/1972 | McCormick | 600/537 |
| 4,152,379 | A | 5/1979 | Suhr | |
| 4,168,706 | A | 9/1979 | Lovell | |
| 4,574,188 | A * | 3/1986 | Midgley et al. | 219/549 |
| 4,753,758 | A | 6/1988 | Miller | |
| 4,971,052 | A * | 11/1990 | Edwards | 128/205.12 |
| 5,121,627 | A * | 6/1992 | D'Aoust | 73/19.05 |
| 5,231,979 | A * | 8/1993 | Rose et al. | 128/204.14 |
| 5,411,474 | A * | 5/1995 | Ott et al. | 604/26 |
| 5,512,732 | A * | 4/1996 | Yagnik et al. | 219/549 |
| 5,857,062 | A | 1/1999 | Bergamaschi et al. | |
| 5,964,223 | A * | 10/1999 | Baran | 128/207.14 |
| 6,010,118 | A * | 1/2000 | Milewicz | 261/142 |
| 6,050,260 | A * | 4/2000 | Daniell et al. | 128/204.22 |
| 6,335,517 | B1 * | 1/2002 | Chauviaux et al. | 219/628 |
| 6,393,919 | B1 * | 5/2002 | Ohji et al. | 73/708 |
| 6,435,180 | B1 * | 8/2002 | Hewson et al. | 128/204.18 |
| 6,584,972 | B2 * | 7/2003 | McPhee | 128/203.17 |
| 6,641,556 | B1 * | 11/2003 | Shigezawa | 604/113 |
| 8,459,259 | B2 * | 6/2013 | Klasek et al. | 128/203.27 |
| 2003/0059213 | A1 * | 3/2003 | Mackie et al. | 392/480 |
| 2003/0132535 | A1 * | 7/2003 | Lipscombe et al. | 261/142 |
| 2003/0141956 | A1 * | 7/2003 | Knutson et al. | 337/299 |
| 2004/0074493 | A1 * | 4/2004 | Seakins et al. | 128/203.16 |
| 2004/0118401 | A1 * | 6/2004 | Smith et al. | 128/204.17 |
| 2004/0149284 | A1 | 8/2004 | Smith et al. | |
| 2004/0250815 | A1 * | 12/2004 | Scott et al. | 128/204.17 |
| 2005/0005937 | A1 * | 1/2005 | Farrugia et al. | 128/204.18 |
| 2005/0132813 | A1 * | 6/2005 | Aratani et al. | 73/715 |
| 2005/0145250 | A1 | 7/2005 | Miyazawa et al. | |
| 2005/0235993 | A1 * | 10/2005 | Baecke et al. | 128/204.18 |
| 2005/0241640 | A1 * | 11/2005 | Baecke et al. | 128/204.23 |

* cited by examiner

HUMIDIFIER FOR RESPIRATORY APPARATUS

This application is the U.S. national phase of International Application No. PCT/AU2007/001715, filed 8 Nov. 2007 which designated the U.S. and claims priority to Australian Patent Application No. 2006906224, filed 8 Nov. 2006, the entire contents of each of which are hereby incorporated by reference.

BACKGROUND OF THE INVENTION

1. Field of the Invention

The present invention relates to humidification and heater arrangements used to control the humidity of breathable gases used in all forms of respiratory apparatus ventilation systems including invasive and non-invasive ventilation, Continuous Positive Airway Pressure (CPAP), Bi-level therapy and treatment for sleep disordered breathing (SDB) conditions such as Obstructive Sleep Apnea (OSA), and for various other respiratory disorders and diseases.

2. Description of Related Art

Respiratory apparatus commonly have devices to alter the humidity of the breathable gas in order to reduce drying of the patient's airway and consequent patient discomfort and associated complications. The use of a humidifier placed between the positive airway pressure (PAP) device (or flow generator) and the patient mask, produces humidified gas that minimizes drying of the nasal mucosa and increases patient airway comfort. In addition in cooler climates, warm air applied generally to the face area in and about the mask, as may occur inadvertently by a leak, is more comfortable than cold air.

Many humidifiers types are available, although the most convenient form is one that is either integrated with or configured to be coupled to the relevant respiratory apparatus. While passive humidifiers can provide some relief, generally a heated humidifier is required to provide sufficient humidity and temperature to the air so that patient will be comfortable. Humidifiers typically comprise a water tub having a capacity of several hundred milliliters, a heating element for heating the water in the tub, a control to enable the level of humidification to be varied, a gas inlet to receive gas from the PAP device and a gas outlet adapted to be connected to a patient conduit that delivers the humidified pressurized gas to the patient's mask.

Typically, the heating element is incorporated in a heater plate which sits under, and is in thermal contact with the water tub.

The humidified air may cool on its path along the conduit from the humidifier to the patient, leading to the phenomenon of "rain-out", or condensation, forming on the inside of the conduit. To counter this, it is known to additionally heat the gas being supplied to the patient by way of a heated wire circuit inserted into the patient conduit which supplies the humidified gas from the humidifier to the patient's mask. Such a system is illustrated in Mosby's Respiratory Care Equipment (7$^{th}$ edition, 2004, ISBN 0-323-022154) at page 97.

Such a heating method for the patient conduit may only provide poor heat transfer due to the wire locating itself along the conduit wall rather than in the main gas stream. A wire will also only give poor turbulent mixing due to its low profile. As a result heat transfer may be poor and the mixing of water vapour and gas may also be poor.

Alternatively the heating wire circuit may be located in the wall of the patient conduit Such a system is described in U.S. Pat. No. 6,918,389.

U.S. Pat. No. 6,918,389 describes a number of humidifier arrangements for supplying low relative humidity, high temperature humidified gas to the patient. Some of these arrangements include pre- or post-heating of the gas to reduce the relative humidity.

None of these prior art devices provides an entirely satisfactory solution to the provision of comfortable humidified gas to the patient, nor to the ease of construction, the hygiene requirements and to the energy and patient comfort requirements at startup.

SUMMARY OF THE INVENTION

The present invention aims to provide an alternative humidifier arrangement which overcomes or ameliorates the disadvantages of the prior art, or at least provides a useful choice.

In one form, the invention provides a respiratory apparatus incorporating a heater tape.

In a further form the invention provides a humidifier incorporating a floating heater plate.

In a further form, the invention provides a humidifier arrangement for respiratory apparatus, including an elongate filament heater in contact with the gas path in the regions before and after the humidification chamber. Preferably, the filament heater in further contact with a body of water in the humidification chamber.

Optionally, heating of the filament is divided into two or more separately controllable zones.

In further form, the invention provides a humidity and/or temperature or other sensing or control apparatus for use with respiratory apparatus, including a heating filament in thermal contact with the gas and/or water, wherein the filament is in the form of an elongate tape. Preferably, the tape is flexible, and may in one embodiment be passed along the bore of the patient gas conduit, or incorporated into the conduit wall.

In a further form, the invention provides a humidifier for use with respiratory apparatus, including a heater in contact with water in the humidification chamber, and where the heater floats or otherwise rises and falls with changes in the water level in the humidification chamber.

A further form of the invention provides a method of humidifying a gas being delivered by a respiratory apparatus to a patient. The method includes the steps of:
 providing a heater in contact with the gas being provided to the patient along a gas flow path and in contact with the water in a humidifier apparatus; and
 providing two or more separately controllable heating zones within the respiratory apparatus.

A further form of the invention provides a method of increasing patient comfort during the start-up of humidification in the respiratory apparatus. The method includes the steps of:
 providing a heater in contact with a gas being provided to the patient along a gas flow path and in contact with water in a humidifier apparatus; and
 commencing heating of the gas in the gas flow path and heating of the water in the humidification apparatus, such that the patient is initially provided with heated gas while the temperature of the water in the humidification apparatus is being increased to the operating temperature.

Preferably, the step of heating the gas in the gas flow path includes the step of heating of a part of the gas flow path upstream of the humidification chamber such that passage of the heated gas through the humidifier apparatus provides an initial degree of humidification.

Further forms of the invention are as set out in the appended claims.

BRIEF DESCRIPTION OF THE DRAWINGS

Further preferred embodiments of the invention will now be described with reference to the accompanying drawings, in which.

DETAILED DESCRIPTION OF PREFERRED EMBODIMENTS

Flexible Tape Heater

Figure 1:
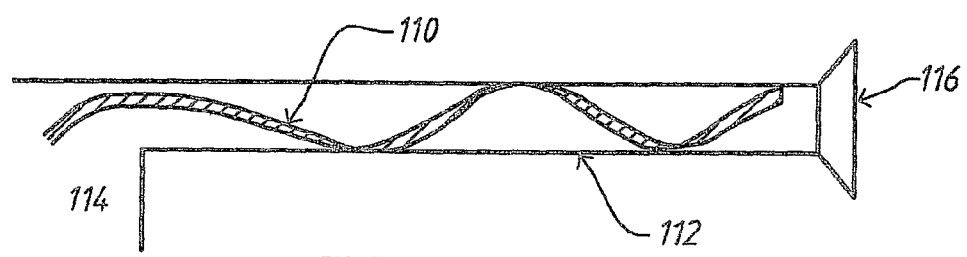
FIG. 1 is a schematic side sectional view of the patient conduit with a flexible tape heater in an embodiment of the present invention.

FIG. 1 illustrates the use of a flexible tape heater 110 as a heating filament within a patient conduit 112 of a respiratory apparatus. The patient conduit 112 is located between the humidification chamber 114 and the patient interface, e.g. mask 116. The patient conduit 112 serves the purpose of conveying the flow of gas from the humidification chamber 114 (partially shown) to the patient mask 116 in respiratory apparatus. The humidification chamber 114 in turn receives pressurized gas from a PAP device (not shown) or flow generator or blower. The humidification chamber 114 is a humidifier that vaporizes water to humidify the gas flow to the patient.

The flexible tape heater 110 in the patient conduit 112 may be used to heat the flow of gas in the patient conduit 112. The thin, flat and extended nature of the flexible tape heater 110 may enhance heat transfer with the gas flow whilst also providing low impedance to the gas flow. Heating of the gas may facilitate the desired temperature and humidity to be reached for the gas delivered to the patient by the respiratory apparatus.

Figure 2:
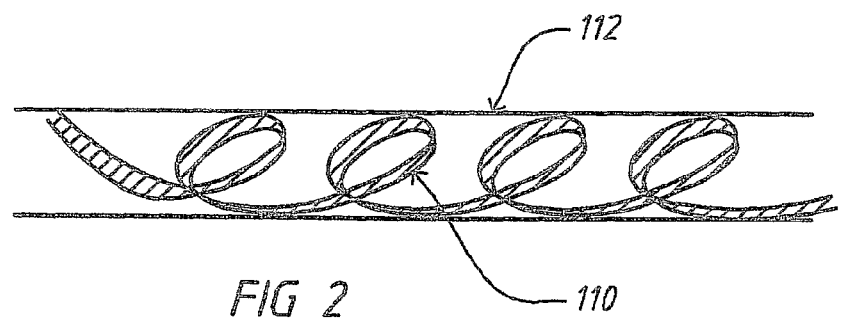
FIG. 2 is an alternative embodiment of FIG. 1 where the flexible tape heater is in a helical configuration.
Figure 3:
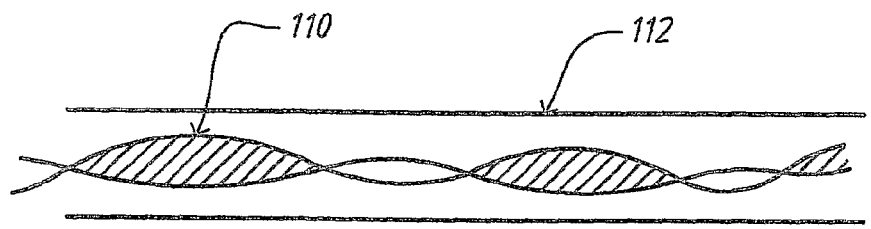
FIG. 3: is an alternative embodiment of FIG. 2 where the flexible tape heater is twisted about its longitudinal axis.

FIGS. 2 and 3 illustrate that the flexible tape heater 110 may be placed in the patient conduit 112 such that the flexible tape heater 110 is twisted or bent about one or more of the flexible tape heater's 110 three axes. FIG. 2 is a helical configuration for the flexible tape heater 110. FIG. 3 illustrates a longitudinal axis twist configuration for the flexible tape heater 110.

The use of these twisted, helical or other configurations described above increases the length of the flexible tape heater 110 in the patient conduit 112 and thus the available surface area for heat transfer between the gas flow and the surface of the flexible tape heater 112. Additionally these configurations can be used to enhance the turbulent mixing of the water vapour produced in the humidification chamber 114 with the gas flow.

In another embodiment an alternate flexible tape heater (not shown) may be combined with the wall of the patient conduit 112 in order to provide heating to the wall to prevent condensation. Optionally an additional flexible tape heater 110 may be used within the patient conduit 112 to provide increased heating to the gas flow. In addition the patient conduit 112 may be insulated or a heated conduit as in the prior art in order to reduce heat loss and minimize consequent water condensation or "rain-out" within the patient conduit 112. The insulation could be an outer sleeve or wrapping about the patient conduit 112. The outer sleeve or wrapping could be foam, fabric or an air space in the case of a double walled conduit.

In an alternate embodiment the patient conduit 112 may be formed by making a helix of the flexible tape heater 110 and joining the edges of the flexible tape heater 110 to form the patient conduit 112.

The flexible tape heater 110 may be sufficiently flexible so that in use flexing of the patient conduit 112 is not restricted. The flexibility of the flexible tape heater 110 may also be sufficient to enable insertion and removal of the flexible tape heater 110 within the patient conduit 112, while being sufficiently stiff so that the flexible tape heater 110 may be inserted into the patient conduit 112 and will support itself in a desired position and not collapse against a wall or to one end of the patient conduit 112. Additionally the stiffness should preferably be sufficient so that the flexible tape heater 110 will not flutter in the gas stream to produce an unwanted audible noise.

In situations where the flexible tape heater 110 is exposed to water the flexibility of the flexible tape heater 110 may allow it to shed precipitates such as Calcium Carbonate (lime scale etc) and various other precipitates commonly found in and derived from mineralised or "hard water". A polytetrafluroethylene (PTFE, "Teflon") coating upon the flexible tape heater 110 may also improve the ability to shed precipitates.

Figure 4:
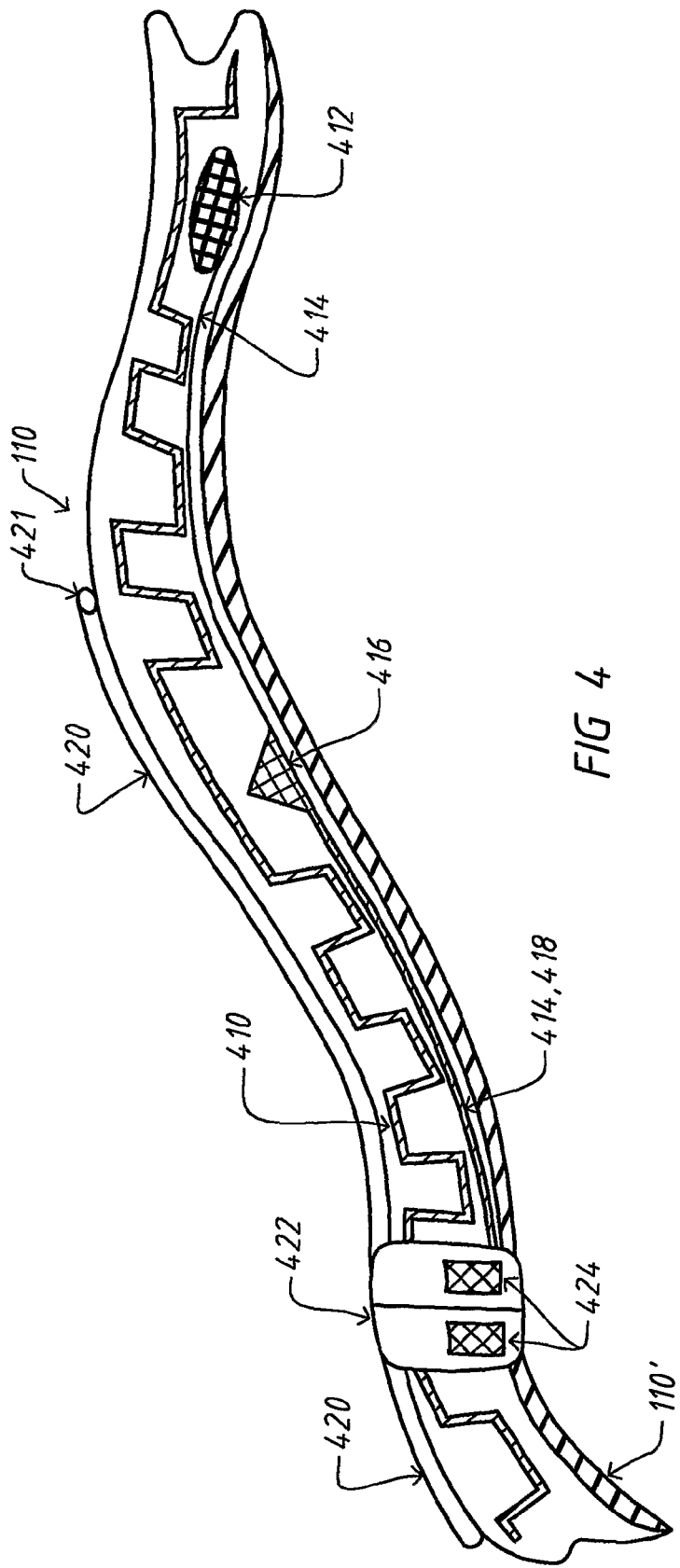
FIG. 4 is a schematic perspective view of another embodiment of the flexible tape heater.

FIG. 4 illustrates one embodiment of the flexible tape heater 110, in which the heater is a heating element 410.

In one embodiment, the heating element 410 is formed by printed circuit techniques applied to a surface of a flexible substrate sheet (not shown) such as kapton, silicone rubber, all-polyimide, PTFE. Included in the printed circuit techniques which may be used are etched foil, printing and vacuum deposition techniques.

Another sheet of the substrate material or other suitable sheet material is then laid upon the substrate sheet with the heating element 410. The two sheets are then adhered or fused together to encapsulate and/or seal the heating element 410 and form a flexible tape heater 110. The Thermofoil™ range of the type of flexible heaters by Minco of Minneapolis USA, described at www.minco.com, are examples of commercially available strip heaters which may be modified for use in the present application.

An alternative embodiment to produce a flexible tape heater 110 is to use a laminator, such as a twin silicon roller laminator, to encapsulate a heating element 410, which may be in the form of wire or ribbon, within two tapes of polycarbonate film. The resulting tape may for example have dimensions ranging from 1 to 10 mm wide and 0.1 to 1 mm thick, although other sizes may be used. Dimensions of about 0.2 to 0.5 mm in thickness and about 5 mm wide are preferred for use in the patient conduit 112.

Alternative profiles or geometric structures for the flexible tape heater 110 may include:
- The transverse cross-section of the flexible tape heater may be rectangular, elliptical or arbitrary.
- The surface of the flexible tape heater 3 may be rough or smooth or dimpled.
- One or more surfaces of the flexible tape heater 3 may be rippled.

In other embodiments the laminating films or encapsulating sheets used to make the flexible tape heater 110 may be of materials such as polyester, polypropylene or any suitable and approved substance for respiratory medicine use. Alternatively, multiple laminating films, sheets or coating films may be used to create a composite strip having the desired properties whilst retaining the desired compatibility with respiratory medicine use for the outer surface. Other conductors may also be present between each of these multiple layers, for example so as to form multiple heating circuits, such as to allow multiple heating zones along the length of the flexible tape heater 110.

A heating element 410 of wire or ribbon may have any suitable transverse cross-section, for example circular, elongate or rectangular. The heating element 410 may for example consist of a resistive conductor.

The arrangement of the heating element 410 between the laminating films or sheets may be any ordered or disordered arrangement that increases the heat transfer of the flexible tape heater 110 to the surrounding media, be it gas or liquid. The heating element 410 may also have a positive thermal coefficient (PTC) for resistance such that heating decreases as the temperature increases towards a desired temperature.

Alternatively the heating element 410 may have a negative thermal coefficient to allow sensing of the temperature or heat transfer of the heating element 410 or surrounding media.

In other embodiments there may be multiple heating element circuits (not shown) within a flexible tape heater 110. The multiple heating elements may be connected in series or parallel. The use of these multiple heating circuits within a flexible tape heater 110 enables additional heating to be applied as required in the operation of the respiratory apparatus.

In another embodiment one or more sensors 412 may be included within the flexible tape heater 110 to monitor characteristics of the gas flow within the respiratory apparatus system. In one embodiment the sensor 412 may monitor air temperature using a sensor such as a thermocouple, platinum resistance thermometer or thermistor with its attendant signal connection 414. It is preferred that the sensor 412 active area (not shown) would be flat with a thickness of less than about 2 mm, and preferably less than 1 mm.

One or more control elements 416 may be included within the flexible tape heater 110 to control characteristics of the gas flow within the respiratory apparatus system. The control element's connection 418 may be separate or multiplexed with the sensor's 412 signal connection 414.

Other active and passive circuit components such as surface mount circuit components (not shown) may also be incorporated within the flexible tape heater 110 as necessary for the proper functioning of the sensing, controlling or heating functions of the flexible tape heater 110. All the circuit components described may exist on a single layer within the flexible tape heater 110 or may be spread over multiple layers of the flexible tape heater 110.

For the flexible tape heater 110 the circuit components all preferably have the common physical feature that they are of a small enough dimension to enable them to be accommodated in the overall profile of the flexible tape heater 110 and co-located with the heating element 410.

The range of sensor 412 and control element 416 components that may be used is shown by way of example in the following:
- Relative and absolute humidity sensors 412.
- Temperature sensors 412 with a positive temperature coefficient (PTC) or negative temperature coefficient (NTC) in the form of a thermistor. Alternatively the PTC property may be intrinsic to the heating element 410 so that the flexible tape heater 110 is self limiting and the heating element 410 is also acting as a control element 416. Thermocouples, platinum resistance thermometers and the like may be used to produce an actual temperature value signal for control and monitoring.
- Directional flow sensing of the gas may realized by using at least two independently controlled heating sections spaced along the flexible tape heater each comprising a temperature sensor (e.g. thermistor). The two or more heating sections are controlled and the temperatures sensed to detect the direction of gas flow.
- Hot wire anemometry for gas flow velocity sensing 412. In an alternate embodiment, a portion at least of the heating element 410 may form the hot wire element for the anemometry sensing system. In use, by way of example, the variation in resistance of the portion of the heating element 410 may provide a measure of gas flow velocity.
- Ambient pressure sensing 412, e.g. inspiratory vs. expiratory pressures.
- Two pressure sensors 412 located respectively at thicker and thinner sections of the flexible tape heater 110 may provide a gas flow rate indication due to the venturi tube effect. A relationship between the outputs of the two pressure sensors 412 provides an indication of gas flow rate or velocity quantities. The venturi tube effect being imparted respectively by the thicker and thinner sections of the flexible tape heater 110 constricting and dilating the gas flow path in the patient conduit 112.
- The pressure sensors 412 may be any one that a person skilled in use of electronic and mechanical pressure sensors or transducers may select that is suitable for the purpose. The pressure sensors 412 may be configured to form a differential pressure sensor for two or more locations within the respiratory apparatus.
- Control elements 416 that make use of the output from a sensor 412, such as for temperature, to control, by way of example a transistor/power controller which regulates the current applied to a heating element 410. A person skilled in the art of electronic control design and manufacture may select from any one of many widely available techniques and devices for control.

Electromagnetic communication protocols via miniature aerials and receivers, e.g. 'Bluetooth'. Aerials for transmitting and receiving information may be located for example in the flexible tape heater 110, the wall of the patient conduit 112, or an active vent system (not shown), or within the other components of a respiratory apparatus (not shown). In another embodiment the aerials could be of a dimension as allowed by the length of the flexible tape heater 110 or the patient conduit 112.

Power supply to a flexible tape heater 110 may be in a similar manner to the electromagnetic communication described above. In this embodiment the transmitting and receiving aerials or inductive coils would be adapted for power transmission.

The flexible tape heater 110 may also comprise one or more micro-tubes 420 to allow remote sensing away from the PAP device and/or humidification chamber 114. The micro-tubes may for example provide pressure, noise/snore and/or cardiological signal sensing. By way of example the micro-tubes may be attached to the side of the flexible tape heater 110 or encapsulated within by one of the manners described above. The micro-tube 420 may have diaphragm 421 at its end that may act as a pressure sensor. The micro-tube's 420 length serving to communicate the mechanical/acoustic pressure signal when the micro-tube 420 wall is comparatively stiff compared with the diaphragm 421. In yet another embodiment a portion of the micro-tube 420 wall (not shown) may serve as a diaphragm for pressure sensing. The use of a micro-tube 420 for pressure signal communication or as part of the pressure sensor may provide the benefit of avoiding flow noise within the patient conduit 112 and other areas in the respiratory apparatus.

In an alternate embodiment the micro-tube 420 may be configured as a differential pressure sensor for two or more locations within the respiratory apparatus. The configuration chosen for one or more micro-tubes 420 may be any one that a person skilled in the use of mechanical and electronic pressure sensors may select that is suitable for the purpose.

In FIG. 4 a tape connector 422 is shown joining two flexible tape heaters 110, 110' to each other. The joining of a number of flexible tape heaters 110 may be to allow electrical and other sensing and controlling communications between the flexible tape heaters 110 as well as power supply. The joining may also offer a way of securing in position a flexible tape heater 110 within a respiratory apparatus. The tape connector 422 may be any one of the connectors widely available or readily designed and manufactured by a person skilled in the art such that the tape connector 422 is adapted to allow the various embodiments of the flexible tape heater to operate from one flexible tape heater 110 to another flexible tape heater 110'.

Figure 5:
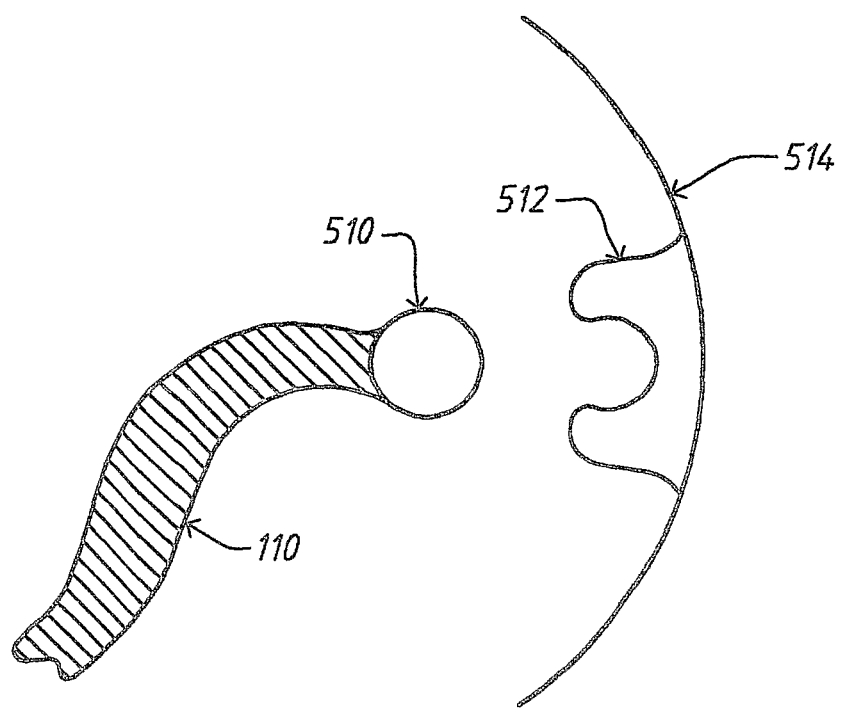
FIG. 5 is a transverse cross-sectional view of the patient conduit showing an embodiment of the flexible tape heater connected to the conduit wall.
Figure 6:
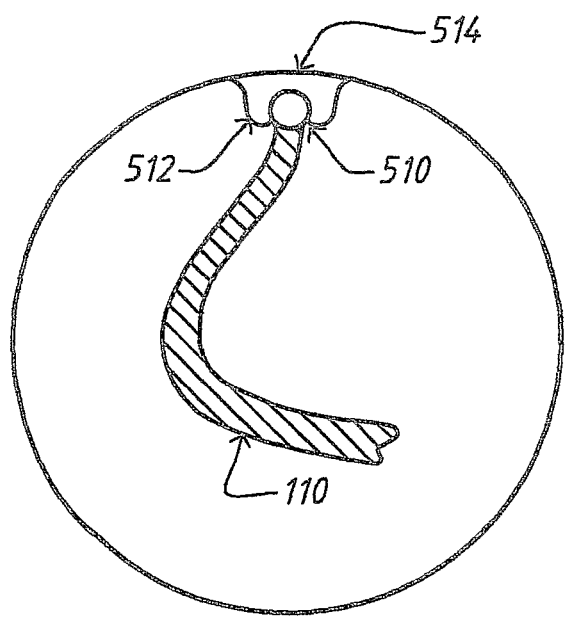
FIG. 6 is another view of the connector embodiment of FIG. 5 where the wall connector is disengaged.
Figure 7:
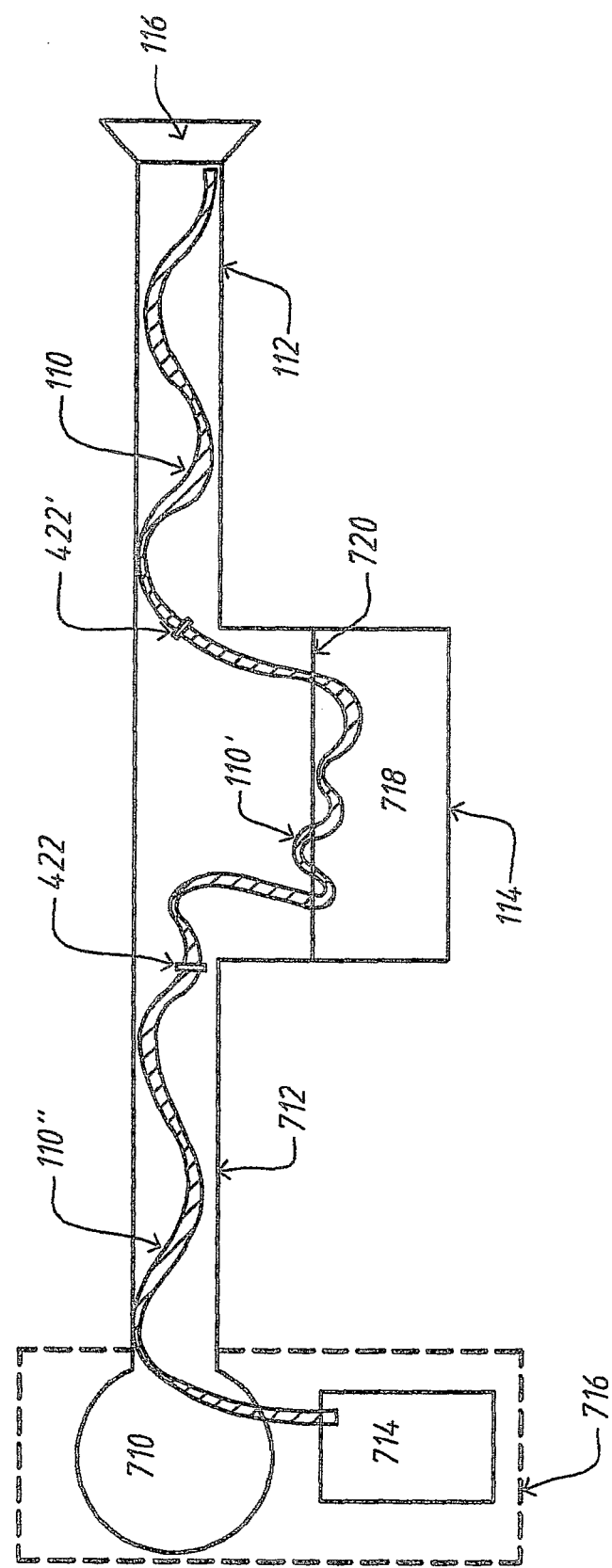
FIG. 7 schematically illustrates a flexible tape heater and humidification arrangement comprising multiple zones within a respiratory apparatus.

FIGS. 5 and 6 illustrate a wall connector 510, 512 which allows the flexible tape heater 110 to attach to the wall 514 of the patient conduit 112 or other suitable internal wall of the respiratory apparatus. The attachment to the wall may be for securing the position of the flexible tape heater 110 or to allow the flexible tape heater 110 to operate with another flexible tape heater 110' and/or to a base unit 716, described below with reference to FIG. 7. Where the wall may have internal electrical wires (not shown), electro-optical fibres (not shown) and mechanical tubes (not shown) to allow a number of flexible tape heaters 110 to operate with each other or the base unit 716 (FIG. 7). The wall connector 510, 512 preferably comprises of compatible male 510 and female 512 connectors which may make an electrical, communications and/or mechanical connection between the flexible tape heater 110 and the wall 514. FIG. 5 shows the male 510 and female 512 wall connectors as a ball and socket arrangement in an engaged configuration, FIG. 6 shows the male 510 and female 512 wall connectors separated. The male 510 and female 512 connectors may be interchangeable in position and engaging action with a mixture of male or female components as a person skilled in the art of connectors may design and manufacture. Preferably the connectors 510, 512 reversibly lock the flexible tape heater 110 in position on the conduit wall 514 such that they may also be disengaged. The connectors 510, 512 may be used at any location along or around a wall of the respiratory apparatus.

The connectors described with reference to FIGS. 4, 5 and 6 may also have Identification-Communication-Memory (ICM) chips 424 as illustrated in FIG. 4. The ICM chips 424 allow the identification and communication of the operating parameters of a flexible tape heater 110 to another flexible tape heater 110' and/or to a base unit 716 described below with reference to FIG. 7. For example, the flexible tape heater 110 may communicate regarding itself as well as detect and report regarding other components that are attached to the respiratory apparatus such as the patient mask 116 type or the patient conduit 112 type or an active vent system (not shown). The information thus gathered by the flexible tape heater 110 may then be sent to the base unit 716 (FIG. 7). The ICM chip 424 system may consist of in part a radio frequency identification chip (RFID) to store and communicate the heating element 410, sensor 412 and control element 416 identification and operating parameters. The base unit 716 (FIG. 7) may have a capability to communicate with the RFID chip and adjust its operation and control of the respiratory apparatus accordingly. Such a system has been described in the Australian Patent Application No. 2005907200 "Identification System and Method for Mask and Ventilator Components", the contents of which are incorporated herein by reference. The communication may also be used to control an active vent system (not shown).

The heating element 410, sensing 412 and control element 416 components described above may be located anywhere along a flexible tape heater 110 or distributed or divided amongst a number of flexible tape heaters 110 as appropriate to their function. For example a thermocouple temperature sensor 412 may be located on a flexible tape heater 110 at the end adjacent the patient mask 116 to enable closed loop temperature control based on the gas temperature delivered to the patient mask 116.

In an alternative embodiment a temperature sensor (not shown) may be located in or in the vicinity of the patient mask 116 but separated from the flexible tape heater 110. However the temperature sensor may communicate with the flexible tape heater 110 in one of the manners described above to enable closed loop control of the temperature of the gas delivered to the patient.

In yet another alternative embodiment different flexible tape heaters 110 may be used for sensing, monitoring and/or controlling the system. Such flexible tape heaters may not include a heating element 410, but instead incorporate one or more other circuit components for sensing 412 and controlling 416. For example a respiratory apparatus may contain two or more flexible tapes, one or more undertaking a heating function and one or more undertaking a sensing and/or controlling function.

The sensing and control methods and devices described above allow closed loop control to be used for optimizing gas delivery to the patient mask 116 so that it is at the desired temperature and humidity. Alternatively a simple open loop system may be used where driving voltages or currents for a heating element 410 may be, by way of an example, from 0.1 to 50 v direct current or the power equivalent for alternating current, for example from 0.1 to 50 W. The sensing and control may also control the level of intentional gas leak from an active vent system, depending on the amount of pressure being supplied. For example as the ventilator pressure increases the active vent system may be controlled to reduce the level of its intentional leak to an acceptable level.

Additionally, the sensors 412 and/or control elements 416 may be used for compliance or statistical data gathering.

Furthermore, the different components of the flexible tape heater 110 embodiments described herein may be used as stand alone components in a respiratory apparatus not employing a humidifier 114, and such arrangements are within the scope of the invention.

A flexible tape heater 110 as thus described would be easily removable from the patient conduit 112 or other sections of a respiratory apparatus to enable cleaning, maintenance or replacement. The flexible tape heater 110 also offers efficient heating with the option of sensing 412 and control element 416 components being easily incorporated into the flexible tape heater 110.

Multiple Zone Heating.

FIG. 7 illustrates a respiratory apparatus which makes use of three flexible tape heaters 110, 110', 110" that are of the same general construction and use as the flexible tape heater 110 embodiments described above.

A PAP device 710 supplies gas supplied from an ambient temperature supply which may be the air in the room or augmented or replaced by a specific gas supply such as oxygen. A flexible tape heater 110" is located in a humidifier conduit 712 which connects the PAP device 710 with the humidification chamber 114. The flexible tape heater 110" located in the humidifier conduit 712 may serve to pre-heat the gas entering the humidification chamber 114 as well as providing any one of the sensing or controlling features described in the above embodiments of the flexible tape heater 110.

The humidifier conduit 712 may be a tube or a short connecting fixture forming a short conduit. In addition the humidifier conduit 712 may be rigid or flexible as required for the operation of the PAP device 710 with the humidification chamber 114 and/or the operation of the flexible tape heater 110". The flexible tape heater 110" is connected to a controller/power supply 714. The controller/power supply 714 supplies power and communication with any heating element 410, sensor 412 or control element 416 of the flexible tape heater 110".

Optionally the controller/power supply 714 may be combined with the PAP device 710 to form a base unit 716.

The flexible tape heater 110" located in the humidifier conduit 712 is connected with a second flexible tape heater 110' located within the humidification chamber 114. The connection between the two flexible tape heaters 110', 110" may be by the tape connector 422 described above with respect to FIG. 4. The flexible tape heater 110' located in the humidification chamber 114 receiving its connection to the controller/power supply 714 via the flexible tape heater 110" located in the humidifier conduit 712.

In an alternate embodiment the flexible tape heater 110' located in the humidification chamber 114 may be connected to the controller/power supply 714 via a wall connector 510, 512 as described above with respect to FIG. 5 and located within the humidification chamber 114. The wall connector 512 being connected to appropriate communication cables and/or tubes (not shown) to the controller/power supply 714.

The flexible tape heater 110' located in the humidification chamber 114 may be wholly or partially within a liquid water 718 body of the humidification chamber 144. The water 718 is provided as a source of water vapour for the humidification of gas passing through the humidification chamber 114. The flexible tape heater 110' may heat the water in the humidification chamber 114 via the use of its heating element 410. The flexible tape heater 110' may also provide any one of the sensing or controlling features described in the above embodiments of the flexible tape heater 110 for the humidification chamber 114.

In an alternate embodiment the flexible tape heater's 110' may be located wholly above the water surface 720. In such a position water vaporization may be imparted via radiation heating and/or convective heating by the flexible tape heater 110' as well as heating the gas within the humidification chamber 114.

A flexible tape heater 110 may also be located in the patient conduit 112 as described above. The flexible tape heater 110 in the patient conduit 112 may be connected via a tape connector 422' to the flexible tape heater 110" in the humidification chamber 114 and thence to the controller/power supply 714 as described above. In an alternate embodiment the flexible tape heater 110 in the patient conduit 112 may be connected with the controller/power supply 714 via a wall connector 510, 512 (as described above with respect to FIG. 5) located within the patient conduit 112.

The flexible tape heater 110 may provide additional heating of the humidified gas in the patient conduit 112 via the use of its heating element 410. The flexible tape heater 110 may also provide any one of the sensing or controlling features described in the above embodiments of the flexible tape heater 110 for the patient conduit 112.

The flexible tape heaters 110, 110', 110" thus may comprise multiple heating circuits, so that each of the three heater zones may be operated independently or in concert. Where the humidifier conduit 712, the humidification chamber 114 and the patient conduit 112 each respectively form a heating, controlling and sensing zone within a respiratory apparatus. The controller/power supply 714 being able to individually and collectively heat, control and sense within each zone. In yet another embodiment a flexible tape heater 110 may have multiple heating elements 410 along it so that temperature and humidity profiles are possible along a flexible tape heater 110 and the regions it occupies in a respiratory apparatus.

In an alternative embodiment one or more of the flexible tape heaters 110, 110', 110" may not be of the type described above but another suitable heating element. For example, the flexible tape heater 110" within the humidifier conduit 712 may be formed as a simple wire heater or other conventional heater type rather than as a flexible tape heater 110 of the type described herein.

The use of the arrangements described above may give the advantages of:

A single inter-connected heating, controlling and sensing system which may be internal to the patient conduit 712, the humidification chamber 114 and the patient conduit 112;

The complete heater, sensor and control system may be removed simply as one connected unit for cleaning, maintenance or replacement;

The interconnection of the flexible tape heaters 110, 110', 110" and the zones facilitates a high degree of closed loop control for temperature and humidity of the gas delivered to the patient.

The ability to sense temperature and humidity at different sections of the patient conduit 112 in order to control the condensation at various sections in the patient conduit 112.

The different components of the heater and/or sensing/control system may be used in combination or separately within a conventional humidifier and an associated respiratory apparatus. For example the flexible tape heater 110 may also be used to heat the patient conduit 112 together with a conventional humidifier with a heating base plate. Alternatively a flexible tape heater 110' may be used to heat the body of water 718 within the humidification chamber 114 together with a heated or insulated wall patient conduit 112, as described above.

The ability to install multiple heaters in parallel and series at any location of the respiratory apparatus. The multiple heaters may exist as multiple flexible tape heaters 110 and/or multiple heating elements 410 within a flexible tape heater 110. This may allow, for example, 'super' heating during the beginning operation of the respiratory apparatus when the body of water 718 requires time to reach the desired temperature. The temporary extra heating of the air with multiple heaters would increase the capacity of the air to take up the cooler water. This may be controlled or profiled in response to the temperature of the water in the body of water 718 to provide the appropriate level of humidity.

For the respiratory apparatus the placement of the three flexible tape heaters 110, 110', 110" and the timing and sequence of their use allows the gas comfort features of temperature and humidity to be managed by allowing the separate, staggered production of:

Heating of an ambient gas that has a low absolute humidity.

Water vaporization.

Heating of the gas that has an increased absolute humidity (after the humidification chamber 114).

The following example of use illustrates an advantage in the operation of the preferred embodiment of FIG. 7.

Particularly in winter and colder climates the patient respiratory gas requires increases in the supplied levels of gas temperature and humidity. In the preferred embodiment the aim of the system from a cold start-up is to rapidly deliver warm gas initially and then increase humidity over time as the humidifier warms up. This approach allows the patient to receive comfortable warm air closely followed by an increasing relative humidity, before there is an onset of any adverse symptoms of low humidity respiratory assistance.

For a cold start in a winter climate the three heater system of FIG. 7 may thus operate in the following manner for the preferred embodiment. Firstly, the cool ambient temperature gas from the PAP device 710 is warmed by using the flexible tape heater 110" in the humidifier conduit 712 with optional additional heating being provided by the flexible tape heater in the patient conduit 110. This initially provides warm but relatively dry air to the patient. However, it is noted that some humidity will be taken up by the warmed gas passing over the water 718 in the humidifier 114.

As the warmed gas flow begins to absorb appreciable water vapour from the unheated water 718 in the humidification chamber 114, the flexible tape heater 110 in the patient conduit 112 may begin or increase its heating in order to prevent 'rain-out' condensation in the patient conduit 112. The initial warming of the gas with the flexible tape heater 110" in the humidifier conduit 712 has the advantage of immediately commencing a degree of humidification, as a simple "pass-over" operation, whilst the flexible tape heater 110' in the humidification chamber 114 is still warming up the water. The heat for vaporization in the simple "pass-over" operation being provided by the heated gas from the humidifier conduit 712.

As the flexible tape heater 110' in the humidification chamber 114 begins to warm the water surface and rapidly increase the absolute humidity in the gas passing through the humidification chamber 114 to achieve the desired level of humidification, the flexible tape heater 110 in the patient conduit 112 would adjust its heating to maintain the absolute humidity by preventing condensation in the patient conduit 112. The flexible tape heater 110 may also serve to maintain the desired gas temperature in the patient conduit 112. The flexible tape heater 110" in the humidifier conduit 712 may have a heating profile based on the level of heating of the body of water 718 in the humidification chamber 114, the heating profile being the rate of heating of the gas flow in a period of time that can be provided by changing the power to the flexible tape heater 110" in the humidifier conduit 712 or the structural configuration of the flexible tape heater 110". In some circumstances there may be more effective control of the humidity by controlling the gas temperature as opposed to heating the water.

An additional advantage of this operational embodiment is that it may allow reduced power consumption at humidification start up so that the respiratory apparatus may be able to be operated by direct current power supply or a portable power supply. Also, satisfactory operation may still be obtained when two or more flexible tape heaters 110 are multiplexed, one flexible tape heater 110 is operated at a time but there is cycling in operation between two or more flexible tape heaters 110.

In addition the various flexible tape heater 110 configurations may be used to provide zones of differing gas flow and/or acoustic properties along the patient conduit 112 or the respiratory apparatus as a whole, FIG. 7.

It may be desirable to modify the acoustic impedance properties of the patient conduit 112 using the flexible tape heater 110 for the following:

the generation or reduction in white noise. (broad frequency spectrum noise);

the damping or filtering of a particular acoustic noise frequency component/s, e.g. structure-borne or air-borne PAP device tonal noise;

enhancement of the propagation of patient respiratory acoustic signals through the patient conduit 112 and to the base unit 716 for monitoring and diagnosis.

The alteration of acoustic impedance properties using the flexible tape heater 110 may be achieved by the choice of the materials making up the flexible tape heater 110 and by the configurations described above for the flexible tape heater 110 in the patient conduit 112, and additionally as shown in FIGS. 1 to 3.

Floating Heater

Figure 8:
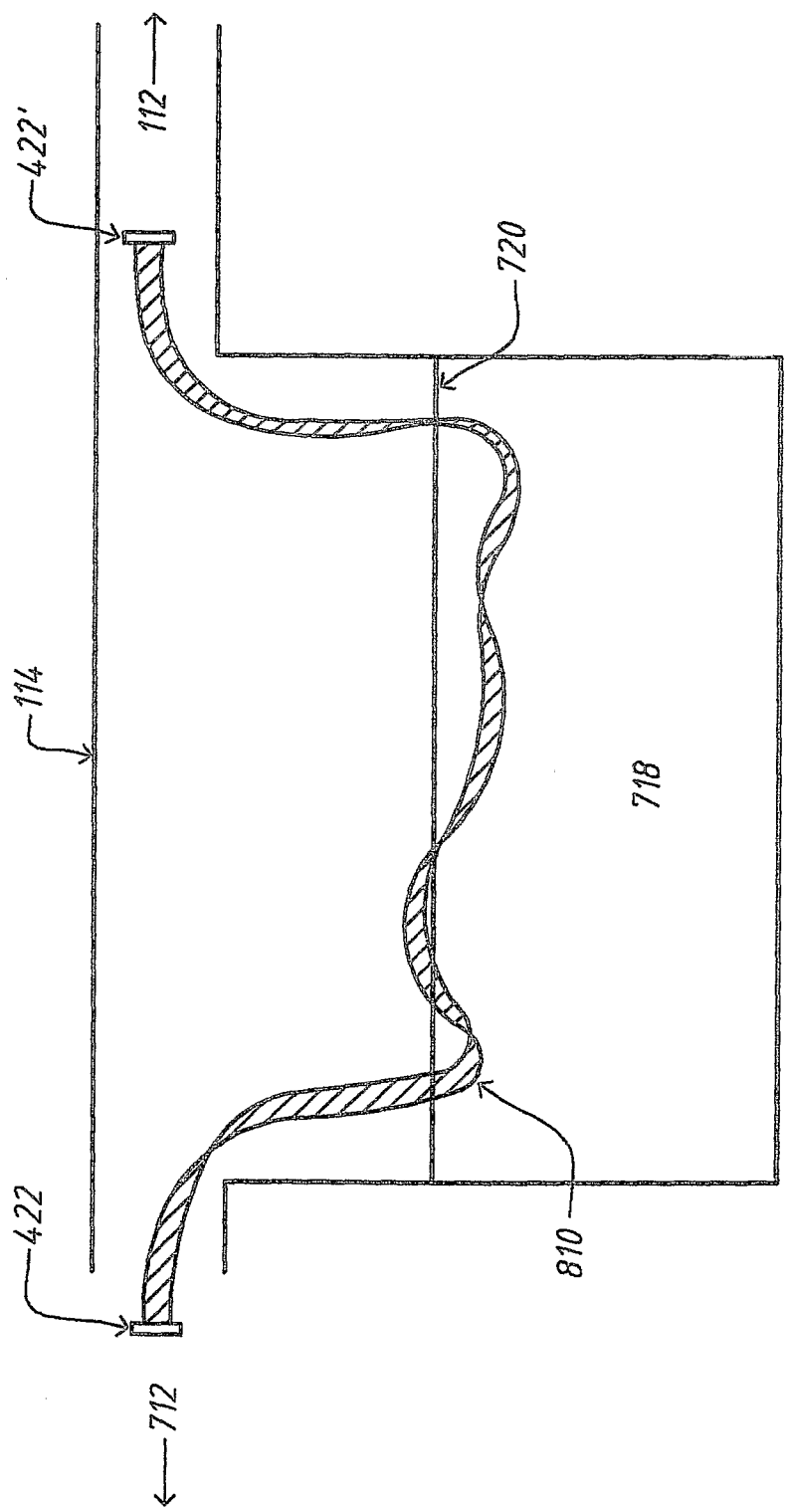
FIG. 8 is a schematic side sectional view of the humidification chamber with an embodiment of the floating heater tape.

In FIG. 8 a humidification chamber 114 arrangement utilizing a floating heater tape 810 is illustrated. The floating heater tape 810 floats in the body of water 718 in the humidification chamber 114 such that a substantial portion of the floating heater tape 810 is immersed but is still adjacent to the water surface 720 so as to heat preferentially that part of the water near the surface 720.

The floating heater tape 810 may comprise a length of flexible tape heater 110 of similar construction and use to that discussed in the above embodiments. This has the significant advantage that the heater for both applications is robust to gas or water immersion, since a floating heater tape 810 may be partially immersed in water during the respiratory apparatus' operation, either unintentionally as the body of water 718 increases or decreases in volume or by tilting of the humidification chamber 114, or intentionally to maintain the temperature of the water vapour in the gas of the humidification chamber 114.

The respective upstream and downstream ends of the floating heater tape 810, respectively located in the humidifier conduit 712 and the patient conduit 112, may have tape connectors 422, 422' so that the floating tape heater 810 may connect with other flexible tape heaters 110 as described in the above embodiments for the respiratory apparatus with respect to FIG. 7. For an alternate embodiment, wall connectors 510, 512 may be used instead of the tape connectors 422, as described above with respect to FIGS. 5 and 6.

The floating heater tape 810 may be adapted to float either by the inherent buoyancy of the floating heater tape 810, by surface tension effects, or may be supported in a manner which keeps the heater near the water surface regardless of changes in the water level. Inherent buoyancy may be obtained by choice of materials or structure, for example voids (not shown) within the floating heater tape 810. A support grid (not shown) may be used to support the floating tape heater near or at the water surface 710. The support grid may also be used as an aid in general positioning of the flexible heater tape 810 within the humidification chamber 114.

Figure 9:
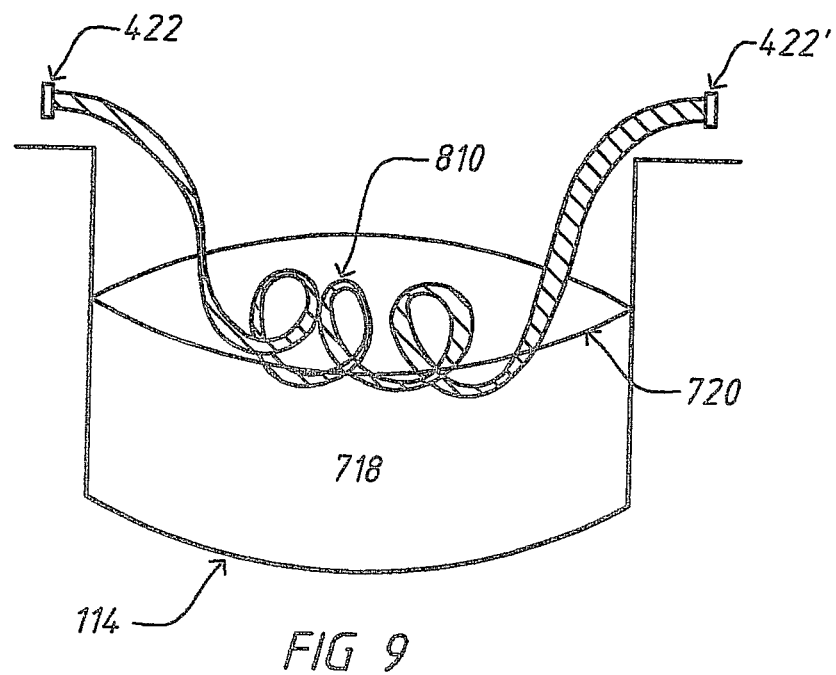
FIG. 9 is a perspective sectional view of another embodiment of a floating heater tape having a helical construction.
Figure 10:
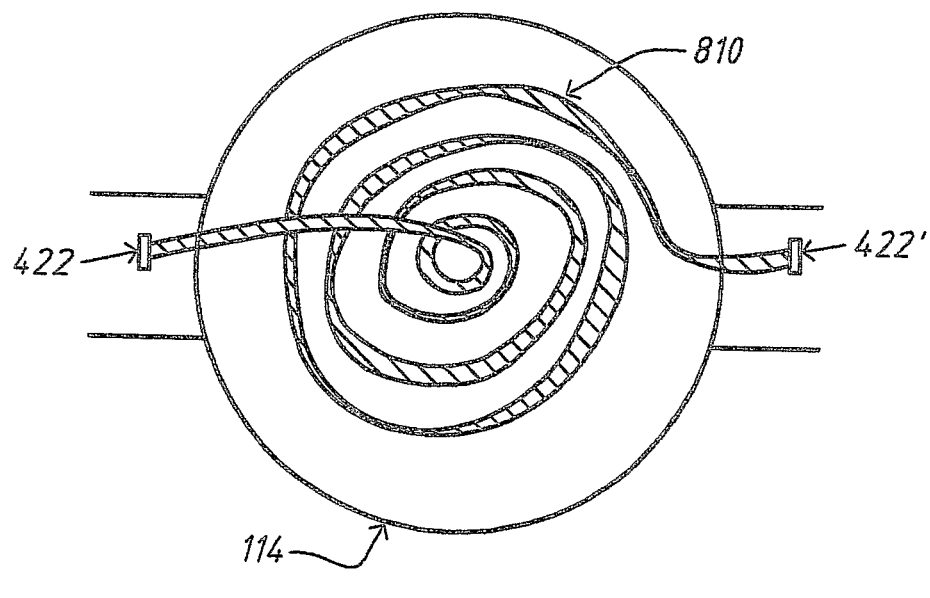
FIG. 10 is a plan view of another embodiment of a floating heater tape wound in a horizontal spiral.

FIGS. 9 and 10 illustrate a number of exemplary embodiments that the floating heater tape 810 may have within the humidification chamber 114. FIG. 9 illustrates a floating heater tape 810 which has been wound into a helix. In this embodiment the floating heater tape 810 may intrinsically float such that a sufficient portion of the floating heater tape 810 is immersed in the body of water 718. FIG. 10 illustrates another embodiment where the floating heater tape 810 may be wound in a horizontal spiral.

The preceding embodiments for the floating heater tape 810 represent a number of defined configurations whereas in use the floating heater tape 810 may assume a combination of the defined or undefined configurations. For example a long helix which continues as a spiral, combining FIGS. 9 and 10. Additionally, the floating tape heater 810 configuration may be spiraled or otherwise formed so as to be partly immersed in the body of water 718 so that it heats both the water near the air and the air near the water, in the proximity of the water surface 720, to produce a stratified zone of heat to improve water uptake into the gas for humidification.

Floating Heater Plate

Figure 11:
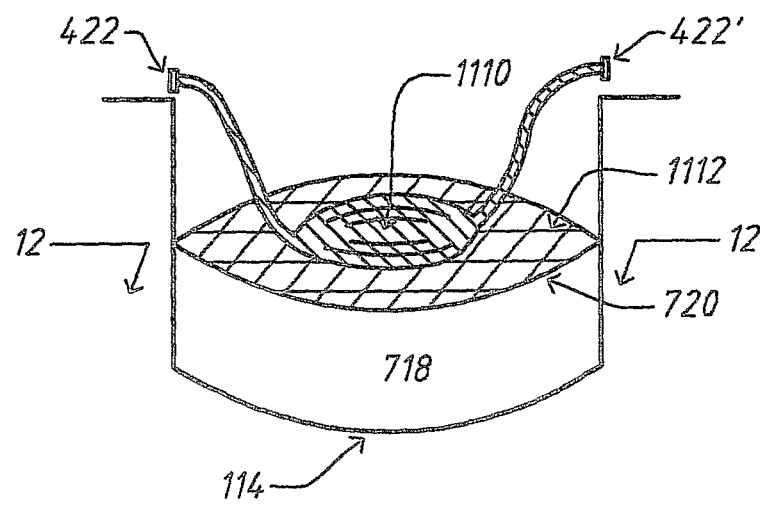
FIG. 11 is a perspective view of an embodiment of a floating heater plate secured to a floating support grid.

FIG. 11 illustrates a floating heater plate 1110 constructed in a similar manner to the floating heater tape 810, described above, but with a plate form rather than a tape form. The floating heater plate 1110 is shown as a circular disc; however it is to be appreciated that the floating heater plate may be formed in any desired shape.

The floating heater plate 1110 may be secured to a floating support grid 1112 or other buoyancy device (not shown), for example a buoyant plastics material. The floating support grid 1112 may facilitate the floating heater plate 1110 to be positioned just below the water surface 720 so as to allow sufficient contact with the water to cause vaporization.

Figure 12:
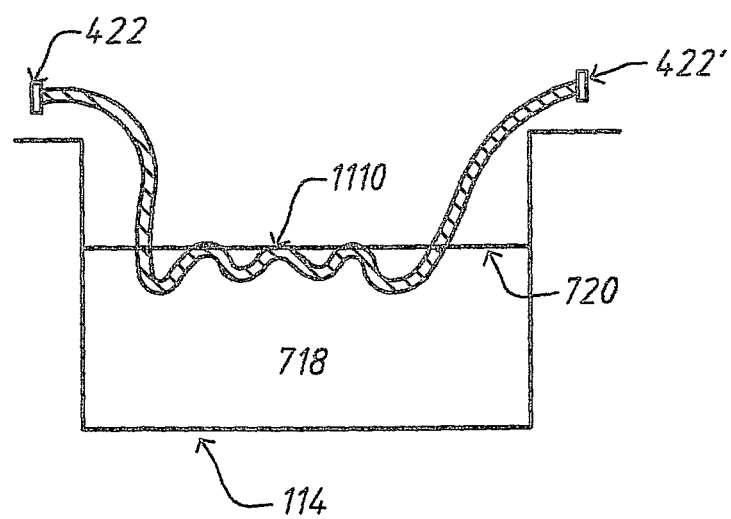
FIG. 12 is side sectional view of another embodiment of FIG. 11, along the plane indicated by 12 on FIG. 11, where the floating heater plate has a rippled or dimpled surface.

FIG. 12 shows another embodiment of the floating plate heater 1110 where the plate form is rippled or dimpled in a regular or irregular fashion. The rippling and/or dimpling provides valleys which may allow pockets of water to accumulate on the upper surface of the floating heater plate 1110. In this embodiment, the floating heater plate 1110 may be naturally buoyant, so that floating heater plate 1110 may float without the need for a support grid 1112 or other buoyancy device.

Figure 13:
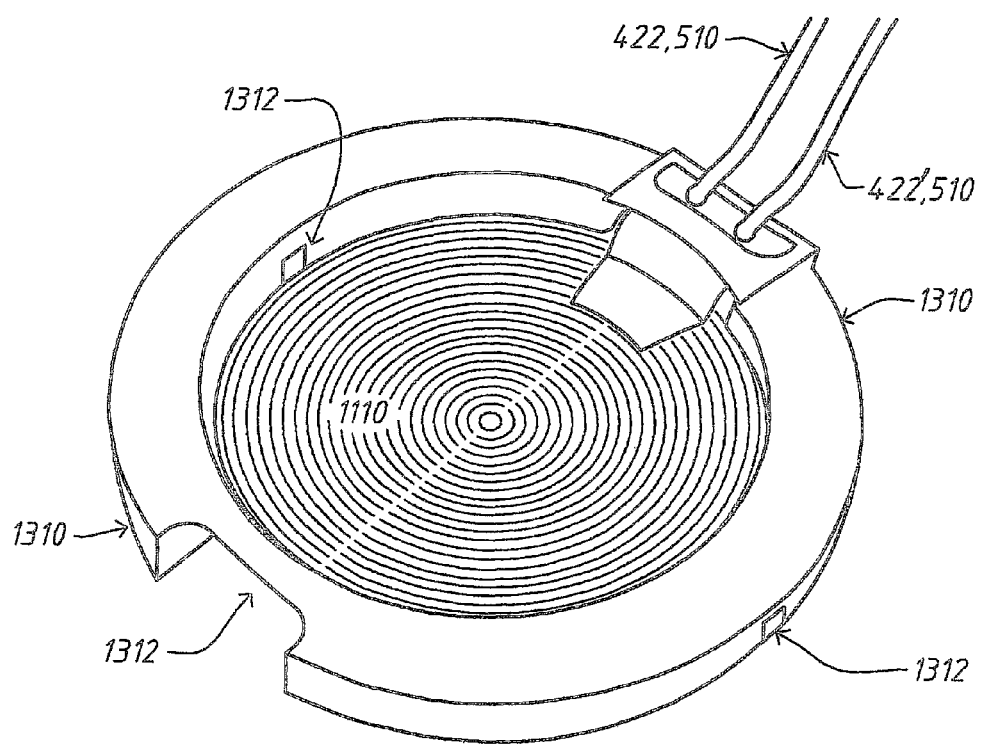
FIG. 13 is a perspective view of another embodiment of the floating heater plate located within a buoyant ring.

In an alternative embodiment shown in FIG. 13, the floating heater plate 1110 is located within a buoyant ring 1310 that allows a shallow bath of water (not shown) to be present above floating heater plate 1110. Apertures 1312 through the buoyant ring 1310 allow water to flow onto the upper surface of the floating heater plate 1110 so that a shallow bath of water is formed. The buoyant ring 1310 with the floating heater plate 1110 floats at the water surface 720 of the body of water 718 of a humidification chamber 114. Connections 422, 422', 510 to the floating heater plate 1110 are made through the buoyant ring 1310.

Figure 14:
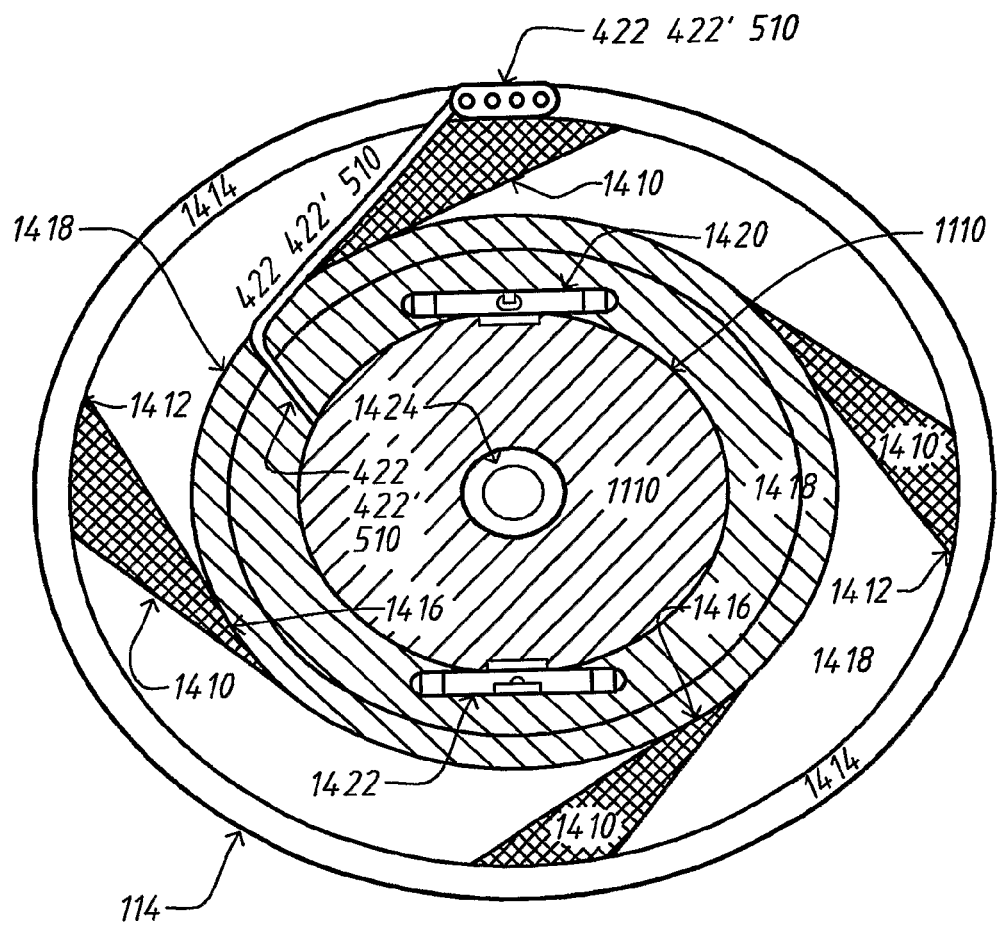
FIG. 14 is a plan, cross-sectional view of another embodiment of the floating heater plate.

FIG. 14 shows another embodiment where the floating heater plate 1110 may also be additionally supported and positioned within the humidification chamber 114 by the use of one or more suspension arms 1410. FIG. 14 is a cross-sectional plan view of the humidification chamber 114 with the floating heater plate 1110. The suspension arms 1410 may be flexibly attached to a suspension line 1412, located where a wall 1414 and a ceiling (not shown) of the humidification chamber 114 meet. The suspension arms 1410 project generally downwards to the floating heater plate 1110. The suspension arms 1410 flexibly attach 1416 preferably to the circumference of a buoyant float 1418 which supports the floating heater plate 1110. Alternatively the suspension arms 1410 may flexibly attach to any other convenient point upon the floating heater plate 1110 or the buoyant float 1418. The suspension arms 1410 may individually comprise of semi-rigid plastic material in a sheet, bar or tape shape. Alternatively the suspension arms 1410 may comprise of lengths of wire or plastic filaments or the same materials in a helical or spring arrangement to form a suspension arm.

A thermal sensor 1420 and a thermal protection switch 1422 is located with the floating heater plate 1110 or may be incorporated within the floating heater plate 1110 in the manner of the sensor 412 and the control element 416 described with respect to the flexible tape heater 110 embodiments above.

The one or more suspension arms 1410 may support the connections 422, 422', 510 between the floating heater plate 1110, the thermal sensor 1420, the thermal protection switch 1422 and the controller/power supply 714.

A position post 1424 is located axially through the center of the floating heater plate 1110 and the buoyant float 1418. The position post 1424 may guide the floating heater plate 1110 as well as providing position information about the water surface 720 or the floating heater plate 1110 to the controller/power supply 714.

Figure 15:
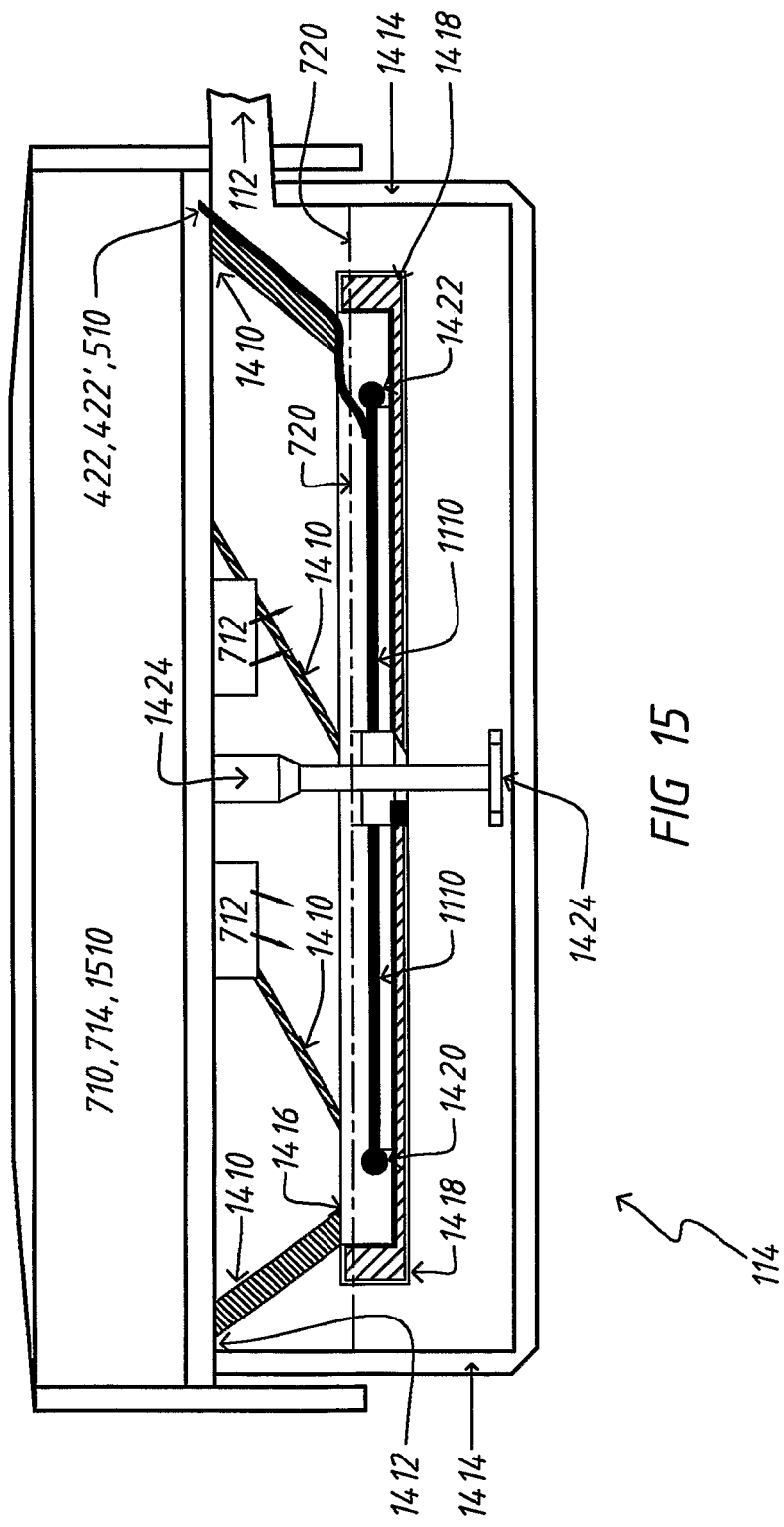
FIG. 15 is a vertical, cross-sectional view of the embodiment of FIG. 14.

FIG. 15 illustrates a vertical cross-sectional view of the FIG. 14 embodiment. This embodiment differs from that of FIG. 7 in that the PAP device 710 and controller/power supply 714 are located as one top unit 1510 on top of the humidification chamber 114. In this configuration the gas flow from the PAP device 710 is directed (as indicated by the arrows) by two humidifier conduits 712 onto the water surface 720. However in alternate embodiments one or more humidifier conduits 712 may be used in a similar manner. Humidified gas exiting the humidification chamber 114 is via the patient conduit 112 as shown.

In use the suspension arms 1410 with the buoyant float 1418 allow the floating heater plate 1110 to rise and fall with the water surface 720. In the embodiment illustrated in FIGS. 14 and 15 the suspension arms 1410 operate such that the floating heat plate 1110 rotates (or twists) about an axis corresponding to the location of the position post 1424. In the alternative embodiments of the suspension arms 1410 described above the floating heater plate 1110 may only move vertically without rotation. The suspension arms 1410 with the position post 1424 maintain the desired position of the floating plate heater 1110 with respect to the water surface 720 within the humidification chamber 114. Preferably the depth of water above the floating heater plate may be from 1 to 5 mm and more preferably 3 to 4 mm. The operation of the suspension arms 1410 with the position post 1424 may continue even if the humidification chamber is tilted up to 20 degrees from the vertical. This offers the advantage that the floating heater plate 1110 may continue to be at least partially immersed in water so as to vaporize sufficient water for humidification when the humidification chamber is tilted from the vertical at large angles.

In yet another embodiment the suspension arms 140 may project from the side walls 1414 of the humidification chamber 114 and attach to the floating heater plate 1110 or buoyant float 1418 as described above. In another alternate embodiment the position post 1424 may be absent, the suspension arms 1410 providing the function of the position post 1424.

The above described embodiments of the floating heater tape 810 and floating heater plate 1110 may be more power efficient in generating water vapour, and more effective in quickly achieving the desired water surface temperature for humidification at start-up of the apparatus. This may be due to the effective heat transfer to the water surrounding the heating element 410. In addition, the water adjacent to the water surface 720 is heated preferentially for vaporization rather than heating the whole body of water 718 from the bottom up of the humidification chamber 114 as in the case of a heater being located at the bottom of the body of water 718.

Although the invention has been herein shown and described in what is conceived to be the most practical and preferred embodiments, it is recognized that departures can be made within the scope of the invention, which is not to be limited to the details described herein but is to be accorded the full scope of the appended claims so as to embrace any and all equivalent assemblies, devices and apparatus.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise, comprised and comprises where they appear.

It will further be understood that any reference herein to known prior art does not, unless the contrary indication appears, constitute an admission that such prior art is commonly known by those skilled in the art to which the invention relates.

The invention claimed is:

1. A respiratory apparatus for delivering gas to a patient, including:
    a PAP device generating a supply of pressurised gas to be delivered to the patient;
    a humidifier configured to a) contain a body of water, b) vaporise at least a portion of the body of water and c) deliver water vapour generated from the body of water to humidify the gas;
    a gas flow path leading from the PAP device to the humidifier and from the humidifier to a patient interface; and
    a heater arranged to be in thermal contact with the gas and the body of water, wherein the heater comprises an elongate heating filament in the form of a tape and a portion of the elongate heating filament is arranged to be buoyantly supported by the body of water when the body of water is contained in the humidifier.

2. A respiratory apparatus according to claim 1 wherein the gas flow path includes a first portion between the PAP device and the humidifier and a second portion between the humidifier and the patient interface, and wherein the heating filament extends along at least part of both said first and second portions of the gas flow path.

3. A respiratory apparatus according to claim 1 wherein said heating filament is configured to be in thermal contact with both the gas in the gas flow path and the body of water when the body of water is contained in the humidifier.

4. A respiratory apparatus according to claim 1 wherein the heating filament has an intermediate portion configured to be in contact with the body of water when the body of water is contained in the humidifier.

5. A respiratory apparatus according to claim 1, wherein the heating filament is configured to be at least partly immersed in the body of water when the body of water is contained in the humidifier.

6. A respiratory apparatus according to claim 1, wherein the heating filament is configured to be in contact with a surface of the body of water when the body of water is contained in the humidifier.

7. A respiratory apparatus according to claim 1, wherein the heating filament comprises a flexible tape.

8. A respiratory apparatus according to claim 7, wherein the heating filament is inserted along a bore of a patient gas delivery conduit.

9. A respiratory apparatus according to claim 7, wherein the heating filament is incorporated in a wall of a patient gas delivery conduit.

10. A respiratory apparatus according to claim 7, wherein the flexible tape forms a portion at least of the gas flow path.

11. A respiratory apparatus according to claim 1, wherein the heating filament comprises a heating element sealed within a flexible tape.

12. A respiratory apparatus according to claim 11, wherein the heating element is laminated within the flexible tape.

13. A respiratory apparatus according to claim 11, wherein the flexible tape includes polycarbonate, polyester and/or polypropylene materials.

14. A respiratory apparatus according to claim 13, wherein the heating element is formed by printing or etching or vacuum deposition techniques, upon at least one side of the material.

15. A respiratory apparatus according to claim 11, wherein the flexible tape includes kapton, silicone rubber, all-polyimide, PTFE and/or mica materials.

16. A respiratory apparatus according to claim 11, wherein the heating element includes a wire or a ribbon.

17. A respiratory apparatus according to claim 1, wherein the heating filament further incorporates one or more sensors.

18. A respiratory apparatus according to claim 17, wherein the one or more sensors includes a temperature sensor, a gas flow sensor and/or a pressure sensor.

19. A respiratory apparatus according to claim 18, wherein the one or more sensors includes an electronic pressure sensor adapted to sense one or more pressure signals.

20. A respiratory apparatus according to claim 19, wherein the one or more pressure signals includes noise, snore, cardiological, flow and/or gas flow path pressure.

21. A respiratory apparatus according to claim 18, wherein the one or more sensors includes a pressure sensor having a tube adapted to communicate one or more pressure signals.

22. A respiratory apparatus according to claim 18, wherein the one or more sensors includes a pressure sensor having a tube with a diaphragm adapted to sense one or more pressure signals.

23. A respiratory apparatus according to claim 18, wherein the one or more sensors includes a pressure sensor configured as a differential pressure sensor for two or more locations within the respiratory apparatus.

24. A respiratory apparatus according to claim 18, wherein the gas flow sensor comprises:
 a first pressure sensor associated with a thick portion of the heating filament; and
 a second pressure sensor associated with a thin portion of the heating filament,
 wherein an indication of a gas flow quantity is derived from a relationship between outputs of the first pressure sensor and the second pressure sensor.

25. A respiratory apparatus according to claim 18, wherein the gas flow sensor comprises at least a portion of the heating filament configured as a hot wire anemometer.

26. A respiratory apparatus according to claim 1, wherein the heating filament further incorporates one or more control elements.

27. A respiratory apparatus according to claim 1, wherein the heating filament is adapted to receive one or more circuit components to monitor or control characteristics of the delivered gas.

28. A respiratory apparatus according to claim 27, wherein said characteristic includes temperature, humidity, gas flow, gas velocity and/or pressure.

29. A respiratory apparatus according to claim 1, wherein the heating filament further incorporates components adapted to enable the heating filament to obtain power from a wall adapted to allow one or more heating filaments to obtain power from a power supply.

30. A respiratory apparatus according to claim 29, wherein the power supply is a base unit.

31. A respiratory apparatus according to claim 1, wherein the heating filament further incorporates components adapted to enable a plurality of said heating filaments to supply power to each other from a power supply.

32. A respiratory apparatus according to claim 1, wherein the heating filament further incorporates components adapted to identify, communicate or have a memory device to enable a plurality of said heating filaments to interact with each other and a base unit.

33. A respiratory apparatus according to claim 32 wherein said heating filament interacts with the base unit via one or more heating filaments.

34. A respiratory apparatus according to claim 32 wherein said heating filament interacts with the base unit via a wall adapted to allow one or more heating filaments to interact with each other and the base unit.

35. A respiratory apparatus according to claim 1, wherein the heating filament is positioned within the gas flow path and is twisted about a longitudinal axis of the filament.

36. A respiratory apparatus according to claim 35, wherein the gas flow path includes a humidifier conduit, the humidifier and/or a patient gas delivery conduit.

37. A respiratory apparatus according to claim 1, wherein the heating filament forms a helix within the gas flow path.

38. A respiratory apparatus according to claim 1, wherein the heating filament is configured to modify acoustic properties of the respiratory apparatus.

39. A respiratory apparatus according to claim 1, including a plurality of said heating filaments.

40. A respiratory apparatus according to claim 39, wherein one or more of said plurality of said heating filaments further comprises one or more sensors or control elements.

41. A respiratory apparatus according to claim 39, wherein said plurality of said heating filaments comprise a plurality of heating circuits.

42. A respiratory apparatus according to claim 1, wherein said heating filament comprises a plurality of heating circuits.

43. A respiratory apparatus according to claim 1, wherein a portion of the heater is in thermal contact with the pressurised gas independently of the water when the humidifier is in an operating orientation.

44. A humidifier for respiratory apparatus, comprising:
 a first respiratory gas passage for receiving gas from a PAP device;
 a humidification chamber adapted to contain water for vaporisation and humidify the gas;
 a second respiratory gas passage for delivering the gas from the humidification chamber to a patient interface; and
 a heater configured to be in direct contact with the gas and configured to be buoyantly supported by the water contained in the humidification chamber, wherein the heater comprises an elongate heating filament in the form of a tape.

45. A humidifier according to claim 44, wherein the heating filament extends along at least part of both said first and second respiratory gas passages.

46. A humidifier according to claim 44, wherein a portion of the heating filament is configured to be in direct contact with the water in the humidification chamber.

47. A humidifier according to claim 44, wherein a portion of the heater that is in the humidification chamber is configured to be at least partially submerged in the water.

48. A humidifier according to claim 44, wherein the humidifier is configured so that the heater in direct contact with the gas and the water when the humidifier is in an operating orientation and the humidifier contains the water.

49. A humidifier for respiratory apparatus, the humidifier comprising:
 a container for holding a body of water, the container comprising a respiratory gas inlet and a respiratory gas outlet;
 apparatus for passing a respiratory gas flow over a surface of the water to humidify the gas flow; and
 a heater supported so as to directly heat the water adjacent and below said surface regardless of a level of water in the humidifier, the heater extending from the respiratory gas inlet to the respiratory gas outlet.

50. A humidifier according to claim 49, wherein the heater is supported so as to float adjacent the surface of the water.

51. A humidifier according to claim 50, wherein the heater is supported by an inherent buoyancy of the heater.

52. A humidifier according to claim 50, wherein the heater is supported by a buoyant support body.

53. A humidifier according to claim 52, wherein the buoyant support body is a plate with one or more apertures.

54. A humidifier according to claim 53, wherein the plate with one or more apertures is a grid or mesh.

55. A humidifier according to claim 49, wherein the heater comprises a flexible tape heater.

56. A humidifier according to claim 55, wherein the flexible tape heater forms a helix in the humidifier.

57. A humidifier according to claim 55, wherein the flexible tape heater forms a spiral in the humidifier.

58. A humidifier according to claim 55 where a portion of the flexible tape heater is in the gas flow and another portion of the flexible tape heater is in the body of water.

59. A humidifier according to claim 55, wherein the flexible tape heater is configured as a plate.

60. A humidifier according to claim 59 wherein the plate is supported by a buoyant support body about a peripheral edge of the plate.

61. A humidifier according to claim 49, wherein a surface of the heater has one or more dimples.

62. A humidifier according to claim 49, wherein the heater surface has one or more ripples.

63. A humidifier according to claim 49, wherein the heater is further supported by one or more suspension arms.

64. A humidifier according to claim 49, wherein the heater is supported so as to directly heat the water immediately below the surface.

65. A humidifier for respiratory apparatus, comprising a first respiratory gas passage configured to receive gas from a PAP device, a humidification chamber configured to humidify the gas, a second respiratory gas passage for delivering the gas from the humidification chamber to a patient interface, and a heater in thermal contact with the gas and buoyantly supported by water in the humidification chamber, wherein the heater comprises an elongate heating filament extending along at least part of both said first and second respiratory gas passages.

66. A humidifier according to claim 65, wherein the heating filament is in thermal contact with water in the humidifier chamber.

67. A humidifier according to claim 65, wherein the heating filament comprises two or more separately controllable heating zones within the respiratory apparatus.

68. A humidifier according to claim 65 wherein the heating filament is a flexible tape heater.

69. A humidifier according to claim 65 wherein a portion of the heating filament is configured as a plate.

70. A humidifier according to claim 65, wherein the heater extends substantially the length of the first respiratory gas passage and the entire portion of the heater extending substantially the length of the first respiratory gas passage is located within the first respiratory gas passage.

71. A respiratory apparatus for delivering gas to a patient, including:
a PAP device configured to generate a supply of pressurised gas to be delivered to the patient;
a humidifier configured to vaporise water and deliver water vapour to humidify the gas;
a gas flow path leading from the PAP device to the humidifier and from the humidifier to a patient interface; and
a continuous heater in thermal contact with the gas and the water, wherein the continuous heater comprises two or more controllable heating zones within the respiratory apparatus,
wherein at least one of said controllable heating zones corresponds to a portion of the continuous heater buoyantly supported by the water.

72. A respiratory apparatus according to claim 71, wherein the heater comprises a plurality of heating filaments in the form of a tape.

73. A respiratory apparatus according to claim 72, wherein each filament corresponds to a respective controllable heating zone of the two or more controllable heating zones.

74. A respiratory apparatus according to claim 73, wherein the gas flow path leading from the PAP device to the humidifier corresponds to a first heating zone, the humidifier corresponds to a second heating zone and the gas flow path leading from the humidifier to the patient interface corresponds to a third heating zone.

75. A respiratory apparatus according to claim 71, wherein the two or more controllable heating zones are controllable from a central location.

76. A method of controlling one or more characteristics of a gas being delivered by a respiratory apparatus to a patient, the respiratory apparatus comprising a humidifier apparatus containing water and a continuous heater in contact with the gas being provided to the patient and the water in the humidifier apparatus, the continuous heater having two or more controllable heater zones, the method including:
controlling the heater zones to control one or more characteristics of the gas within the different zones of the respiratory apparatus to provide gas to the patient with desired one or more characteristics,
wherein at least one of said controllable heater zones corresponds to a portion of the continuous heater buoyantly supported by the water.

77. A method according to claim 76, wherein said one or more characteristics includes temperature, humidity, gas flow, gas velocity and/or pressure.

78. A method according to claim 76, wherein the heater zones are controlled from a central location.

79. A method of increasing patient comfort during start-up humidification of a gas being delivered by a respiratory apparatus to a patient, the respiratory apparatus comprising a heater in contact with the gas being provided to the patient along a gas flow path and in contact with water in a humidifier apparatus, the method including:
commencing heating of the gas in the gas flow path and heating of the water in the humidification apparatus, such that the patient is initially provided with heated gas while a temperature of the water in the humidification apparatus is being increased and before the temperature of the water reaches operating temperature,
wherein the step of heating the gas in the gas flow path includes the step of temporarily providing a higher level of heating of the gas during an initial start-up stage of humidification.

80. A method according to claim 79, wherein the step of heating the gas in the gas flow path includes the step of heating at least a part of the gas flow path upstream of the humidification apparatus such that passage of the heated gas through the humidification apparatus provides an initial degree of humidification.

81. A method according to claim 79, wherein during the commencing of the heating of the gas in the flow path, the gas is directly heated by a heater.

82. A method according to claim 79, wherein heat for vaporizing the water during start-up is provided by the heated gas in the gas flow path.

* * * * *